US006661519B2

(12) United States Patent
Fukasawa

(10) Patent No.: US 6,661,519 B2
(45) Date of Patent: Dec. 9, 2003

(54) SEMICONDUCTOR IMPURITY CONCENTRATION TESTING APPARATUS AND SEMICONDUCTOR IMPURITY CONCENTRATION TESTING METHOD

(75) Inventor: Ryoichi Fukasawa, Yuzukami-mura (JP)

(73) Assignees: Tochigi Nikon Corporation, Otawara (JP); Nikon Corporation, Tokyo (JP)

( * ) Notice: Subject to any disclaimer, the term of this patent is extended or adjusted under 35 U.S.C. 154(b) by 0 days.

(21) Appl. No.: 09/881,738

(22) Filed: Jun. 18, 2001

(65) Prior Publication Data

US 2002/0005951 A1 Jan. 17, 2002

(30) Foreign Application Priority Data

Jun. 20, 2000 (JP) ........................................ 2000-184407

(51) Int. Cl.[7] ............................................... G01N 21/00
(52) U.S. Cl. .................... 356/432; 356/433; 356/370; 438/16
(58) Field of Search ................. 356/432, 433, 356/370; 438/16

(56) References Cited

U.S. PATENT DOCUMENTS

| 5,007,741 A | * | 4/1991 | Carver et al. | ............... 356/448 |
| 5,478,777 A | * | 12/1995 | Yamazaki | ................... 437/173 |
| 5,623,145 A | * | 4/1997 | Nuss | .......................... 250/330 |
| 5,789,750 A | * | 8/1998 | Nuss | ......................... 250/338.1 |
| 6,057,928 A | * | 5/2000 | Li et al. | ..................... 356/445 |
| 6,075,836 A | * | 6/2000 | Ning | ....................... 378/98.12 |

OTHER PUBLICATIONS

Lau, "Infrared Characterization for Microelectronics", World Scientific, 1999.
"Imaging With Terahertz Waves"; B.B. Hu et al., Optics Letters vol. 20, No. 16, pp. 1716–1719; (1995).
"Two–Dimensional Electro–Optic Imaging of THz Beams"; Q. Wu et al. Appl. Phys. Lett. 69 Vol 69, No. 8, pp. 1026–1028; (1996).

* cited by examiner

Primary Examiner—Diane I. Lee
Assistant Examiner—Daniel A. Hess
(74) Attorney, Agent, or Firm—Oliff & Berridge, PLC

(57) ABSTRACT

A semiconductor impurity concentration testing apparatus includes a terahertz pulse light source that irradiates terahertz pulse light on a semiconductor material, a light detector that detects transmitted pulse light having been transmitted through the semiconductor material, a measurement device that ascertains a spectral transmittance based upon a time-series waveform of the electric field intensity of the transmitted pulse light and an arithmetic operation unit that calculates an impurity concentration in the semiconductor material based upon the spectral transmittance. By adopting such a structure, it becomes possible to measure and test the impurity concentration over the entire semiconductor material in a simple manner and to reproduce an image of the impurity distribution.

4 Claims, 14 Drawing Sheets

TERAHERTZ PULSE LIGHT

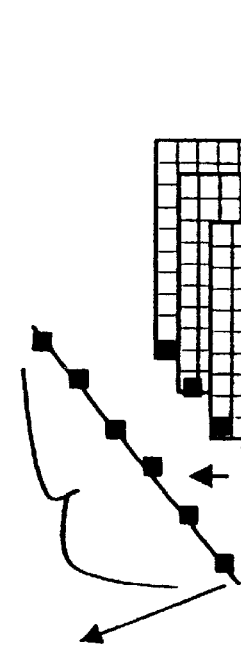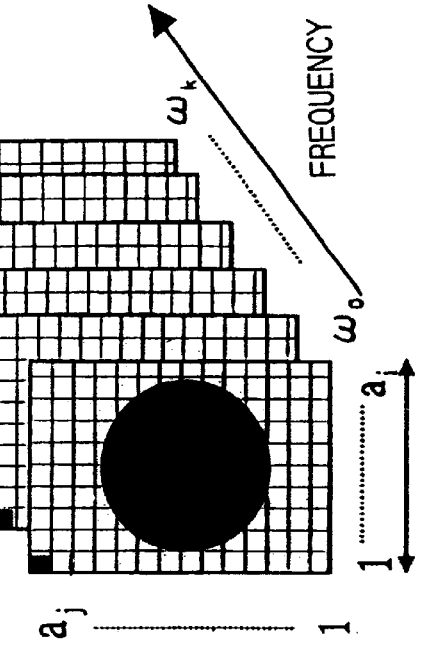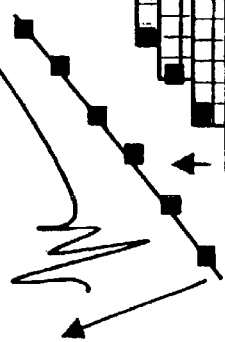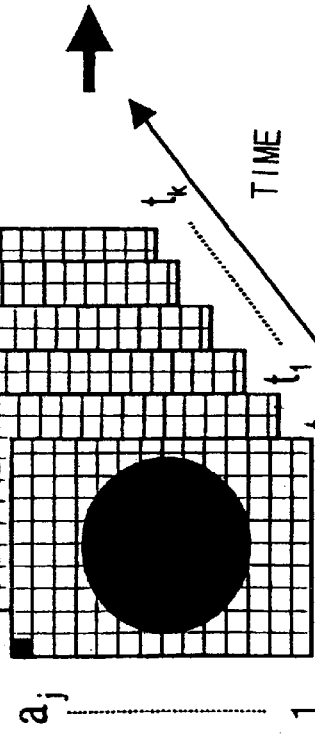

SEMICONDUCTOR IMPURITY CONCENTRATION TESTING APPARATUS AND SEMICONDUCTOR IMPURITY CONCENTRATION TESTING METHOD

INCORPORATION BY REFERENCE

The disclosure of the following priority application is herein incorporated by reference: Japanese Patent Application No. 2000-184407 filed Jun., 20, 2000.

BACKGROUND OF THE INVENTION

1. Field of the Invention

The present invention relates to a testing apparatus and a testing method that enable non-destructive and non-contact measurement of impurity concentration in a semiconductor material such as a semiconductor wafer, an ingot or an epitaxial grown film and, more specifically, the distribution of the oxygen concentration, the nitrogen concentration and the carbon concentration in the semiconductor material and imaging of the distribution of the impurity concentration thus measured.

2. Description of Related Art

In the semiconductor device industry, impurity concentration such as the oxygen concentration, the nitrogen concentration and the carbon concentration with respect to the impurities contained in the semiconductor material used to manufacture a device are crucial factors that determine the performance of the semiconductor device. Conventionally, the measurement of these impurity concentration is implemented through the Fourier transform infrared spectrophotometry. In Fourier transform infrared spectrophotometry impurity concentration are measured based upon the spectral information obtained by irradiating infrared light on a testpiece.

In the Fourier transform infrared spectrophotometric method adopted in the prior art, measurement can be performed only at one point of a semiconductor material through a single measuring operation, and thus, it takes a great deal of time to complete the measurement of the entire semiconductor material. In addition, it is extremely difficult to achieve imaging of the concentration for viewing the impurity quantity distribution at once. Furthermore, it is virtually impossible to capture a spatial image of the impurities in the entire semiconductor material with a resolution in the order of the light wavelength in the practical application.

SUMMARY OF THE INVENTION

An object of the present invention is to provide an impurity concentration testing apparatus and an impurity concentration testing method that enable reproduction of the impurity distribution by measuring and checking the impurity concentration in the entire semiconductor material in a simple manner.

The semiconductor impurity concentration testing apparatus according to the present invention comprises a terahertz pulse light source that irradiates terahertz pulse light onto a semiconductor material, a light detector that detects transmitted pulse light having been transmitted through the semiconductor material, a measurement device that obtains a spectral transmittance based upon a time-series waveform of the electric field intensity of the transmitted pulse light detected by the light detector and an arithmetic operation unit that calculates an impurity concentration in the semiconductor material based upon the spectral transmittance.

The arithmetic operation unit may execute an analysis to calculate the oxygen concentration, the nitrogen concentration and the carbon concentration in the semiconductor material based upon Lambert's light absorption theory.

The semiconductor impurity concentration testing apparatus according to the present invention may further comprise an image processing device that renders the impurity concentration parameters into a two-dimensional image as a spatial distribution.

In addition, the semiconductor impurity concentration testing apparatus according to the present invention may perform two-dimensional scanning of the surface of the semiconductor material with a condensed terahertz pulse light flux or it may two-dimensionally detect transmitted pulse light having been transmitted through the semiconductor material with the light detector by irradiating an expanded light flux of the terahertz pulse light in a batch on the semiconductor material.

In the semiconductor impurity concentration testing method according to the present invention, a condensed light flux of terahertz pulse light is irradiated onto the semiconductor material, the condensed light flux and the semiconductor material are caused to move relative to each other on the surface of the semiconductor material, transmitted pulse light having been radiated through various points of the semiconductor material is sequentially detected, a spectral transmittance is calculated based upon a time-series waveform of the electric field intensity of the transmitted pulse light and an impurity concentration in the semiconductor material is calculated based upon the spectral transmittance.

Alternatively, in the semiconductor impurity concentration testing method according to the present invention, an expanded light flux achieved by expanding a terahertz pulse light flux is irradiated at once over the entire surface of the semiconductor material, transmitted pulse light having been transmitted through the semiconductor material irradiated with the expanded light flux is detected at once, and a spectral transmittance is calculated based upon a time-series waveform of the electric field intensity of the transmitted pulse light and then an impurity concentration in the semiconductor material is calculated based upon the spectral transmittance.

In either of these semiconductor impurity concentration testing methods, the spectral transmittance is calculated based upon a time-series waveform of the electric field intensity measured by inserting the semiconductor material in the optical path in which the transmitted pulse light is detected and a time-series waveform of the electric field intensity measured without inserting the semiconductor material in the optical path.

BRIEF DESCRIPTION OF THE DRAWINGS

FIG. 3A shows time-series transmitted images obtained by the impurity concentration testing apparatus in the embodiment and FIG. 3B shows the spectral characteristics;

DETAILED DESCRIPTION OF THE PREFERRED EMBODIMENTS

The impurity concentration testing apparatus according to the present invention irradiates pulse light in the terahertz frequency range on a semiconductor material, detects the transmitted pulse light and obtains the spectral transmittance through an arithmetic operation to calculate impurity concentration in the semiconductor material. A spatial image representing the impurity concentration in the semiconductor material may be reproduced at a resolution corresponding to the order of the light wavelength, based upon a two-dimensional distribution of the transmitted pulse light, i.e., based upon transmitted images. In more specific terms, the distribution of the electric field intensity is measured from the transmitted images and a Fourier transform is performed on the results of the measurement to obtain a two-dimensional projected image (a spectral image) at each frequency setting. By analyzing the spectral images, the impurity concentration distribution in the semiconductor material is measured and checked. The analysis may be performed based upon Lambert's light absorption theory, which is to be detailed later.

It is desirable to use terahertz pulse light within a frequency range of $0.1 \times 10^{12} \sim 80 \times 10^{12}$ Hz in the impurity concentration testing apparatus according to the present invention.

The photometric optical system employed to obtain transmitted images of a semiconductor material by using terahertz pulse light may be either a scanning-type imaging optical system or a non-scanning-type optical system.

Figure 1:
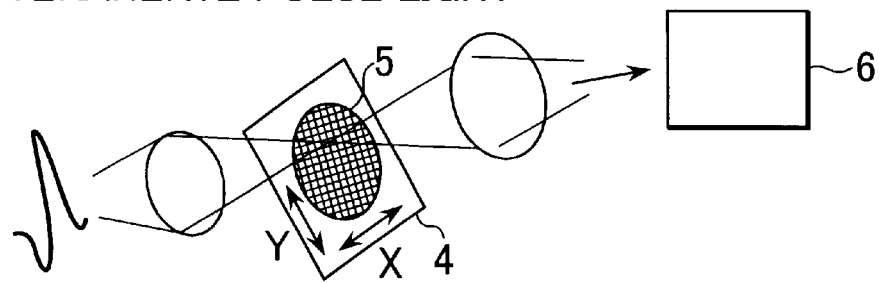
FIG. 1 is a schematic diagram illustrating the scanning-type imaging photometric method adopted in the impurity concentration testing apparatus in an embodiment according to the present invention.

FIG. 1 is a schematic diagram illustrating a scanning imaging photometric method in which the semiconductor material is irradiated with terahertz pulse light condensed at one point of the semiconductor material. The condensed light flux irradiated on the semiconductor material 5 is transmitted through the semiconductor material 5 and enters a terahertz pulse detector 6. The terahertz pulse detector 6 includes a light-receiving surface which corresponds to one pixel. The terahertz pulse detector 6 receives the transmitted pulse light having been transmitted through one point of the semiconductor material 5 and outputs a signal indicating the electric field intensity of the transmitted pulse light.

A mechanical scanning system 4 (e.g., an X-Y stage) is employed to scan the semiconductor material 5 along the X-Y plane (see FIG. 1), and the terahertz pulse detector 6 sequentially receives the transmitted pulse light. By implementing such X-Y scanning, the electric field intensity level corresponding to the transmitted pulse light having been transmitted through each point of the semiconductor material 5 is obtained, and the individual electric field intensity levels are spatially synthesized to obtain a two-dimensional image. Instead of implementing X-Y scanning on the semiconductor material 5, the optical system that irradiates terahertz pulse light on the semiconductor material 5 and the optical system that guides the transmitted pulse light to the terahertz pulse detector 6 may be engaged in an interlocking operation. By providing such a mechanical scanning system, the test area in the semiconductor material can be freely selected.

The following is an explanation of a method that may be adopted to obtain a transmitted image. The semiconductor material 5 is first placed on the mechanical scanning system 4. By scanning the semiconductor material 5 along the X-Y plane almost perpendicular to the optical axis of the condensed light flux with the mechanical scanning system 4, the electric field intensity corresponding to each pixel is measured. As the electric field intensity levels of the individual pixels are sequentially measured, the electric field intensity distribution of the transmitted pulse light within the X-Y plane in the semiconductor material 5 is obtained.

Figure 2A:
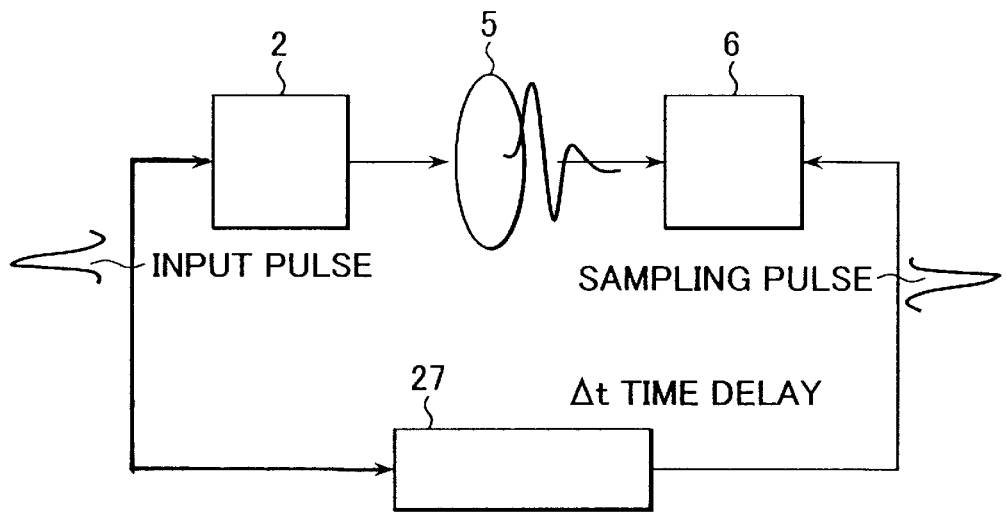
FIG. 2A is a block diagram illustrating the principle of the time-series waveform measurement and FIG. 2B is a graph presenting an example of a time-series waveform.
Figure 2B:
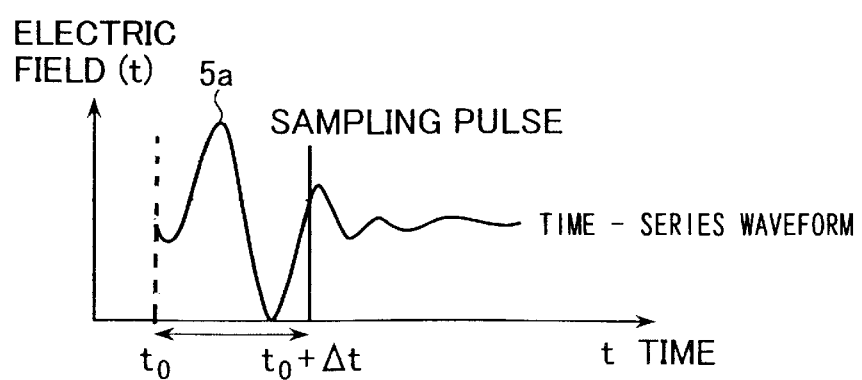

Next, a method through which the time-series waveform of the electric field is measured with a measurement device is explained. FIG. 2A is a block diagram provided to illustrate the principle of the time-series waveform measurement, and FIG. 2B is a graph presenting an example of a time-series waveform. At a time point t0, pulse light (terahertz pulse light) is irradiated from a terahertz pulse light source 2 in response to an input pulse, and the transmitted pulse light having been transmitted through the semiconductor material 5 reaches the terahertz pulse detector 6. The input pulse, which is to be detailed later, is a laser pulse that is input to the terahertz pulse light source 2 in order to generate terahertz pulse light.

The input pulse is also sent to the terahertz pulse detector 6 via a time-delay device 27 which is to be explained later, as a sampling pulse to be used to start to measure the electric field intensity of the terahertz pulse light. The terahertz pulse detector 6 reads out the electric field intensity of the transmitted pulse light at the corresponding time point. With the timing with which the sampling pulse is supplied retarded by an interval Δt by the time-delay device 27, the terahertz pulse detector 6 reads out the intensity of the electric field at a time point t0+Δt.

FIGS. 3A and 3B are conceptual diagrams provided to illustrate the principle applied when obtaining the spectral characteristics from time-series transmitted images. With the time delay Δt to be achieved by the time-delay device 27 set at 0, the electric field intensity of transmitted pulse light is measured by scanning the semiconductor material 5 along the X-Y plane over the number of times corresponding to the total number of pixels, i.e., i×j times. As a result, the image of the electric field intensity distribution within the X-Y plane at the time point t0 is obtained.

The image of the electric field intensity distribution within the X-Y plane at a time point t1 is obtained by measuring the electric field intensity over i×j times as described above, with t1 representing the delayed time point t0+Δt resulting from the time delay Δt achieved through the time-delay device 27. By varying the length of the time delay Δt, the electric field intensity distribution within the X-Y plane at any time point can be measured. By viewing the numerical value data of the transmitted images for a given pixel (aij) thus obtained along the time axis, a time-series waveform E(t, i, j) spanning the time points t0~tk is obtained as shown in FIG. 3A. The use of the time-delay device 27 allows the change occurring in the electric field intensity distribution of the transmitted pulse light within the X-Y plane over time to be viewed as if it were a dynamic image.

Through the operation described above, the time-series waveform E(t,i,j) of the electric field intensity corresponding to each pixel is obtained. By performing a Fourier transform arithmetic operation on the time-series waveform E(t, i, j) corresponding to each pixel (aij), spectral characteristics E(ω, i, j) of the semiconductor material 5 at each pixel (aij) are ascertained as shown in FIG. 3B. By restructuring the numerical value data on a computer, electric field intensity images within the X-Y plane over the frequency range of ω0 through wk, i.e., two-dimensional projected images (spectral images), are obtained. The information related to impurity concentration within the semiconductor material is contained in this series of two-dimensional projected images. By analyzing such information, the images can be converted to two-dimensional projected image information related to the impurity concentration in the semiconductor material by adopting Lambert's light absorption theory to be detailed later.

Figure 4:
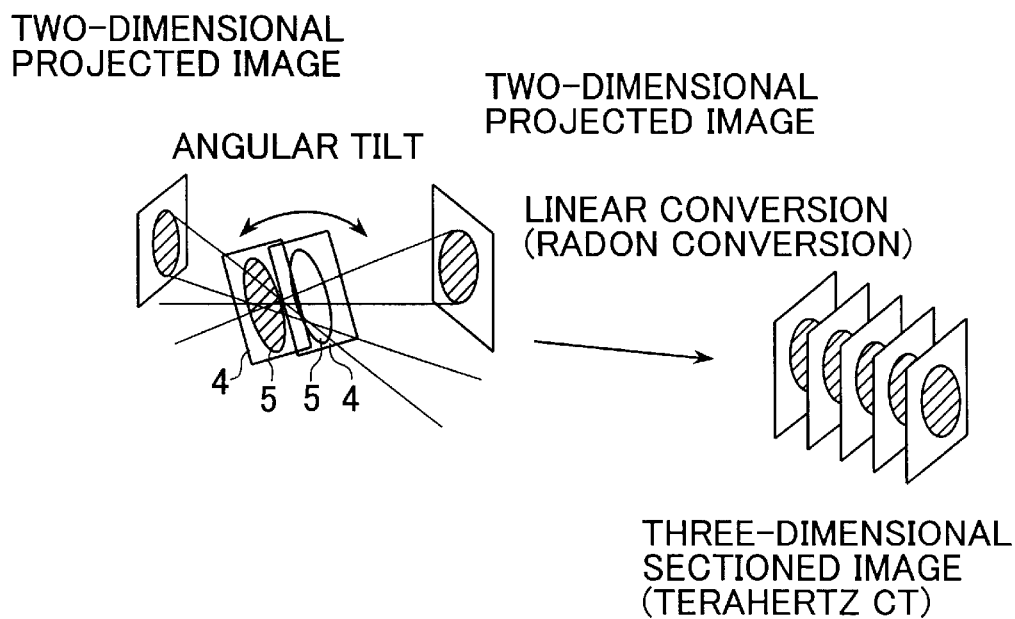
FIG. 4 is a conceptual diagram illustrating the process of obtaining a three-dimensional sectioned image.

The angle of the terahertz pulse light irradiated on the semiconductor material may be varied to obtain various two-dimensional projected images corresponding to the individual angles to obtain a three-dimensional sectioned image with these two-dimensional projected images. FIG. 4 is a conceptual diagram illustrating the process through which a three-dimensional sectioned image is obtained from a plurality of two-dimensional projected images. The angle at which the semiconductor material 5 is irradiated with the terahertz pulse light may be changed by providing a tilt mechanism as an integrated part of the X-Y stage 4 or by providing a separate tilt mechanism. The computer is engaged in a linear conversion operation such as Radon conversion by using a plurality of two-dimensional projected images obtained at varying tilt angles to obtain a three-dimensional sectioned image. This process may be considered to be terahertz CT (computerized tomography). The Radon conversion refers to a method through which one-dimensional projection data are measured and a two-dimensional section of the original object is restructured from the measured data, or two-dimensional projection data are measured and a three-dimensional distribution in the original object is restructured based upon the measured data (see "Image Data Processing" compiled by Sou Kawada and Shigeo Minami, published by CQ Publishing Company).

Figure 5:
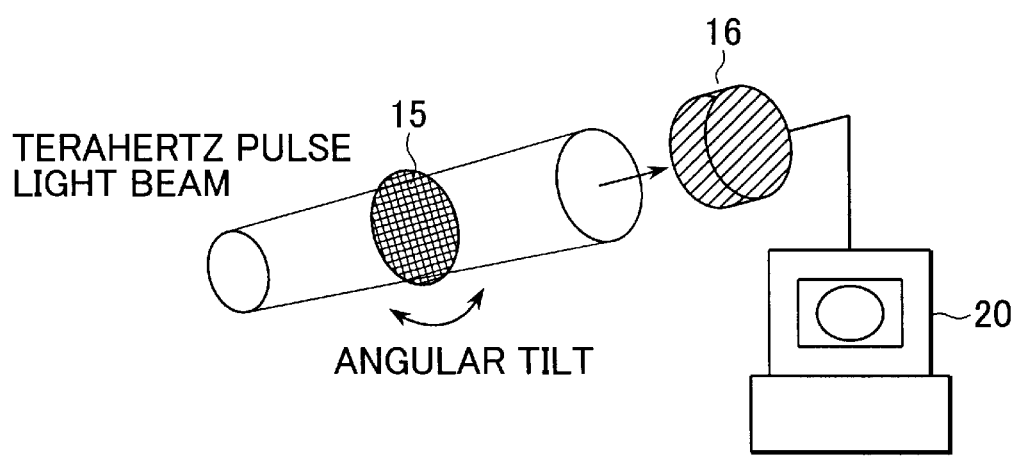
FIG. 5 is a schematic diagram illustrating the non-scanning-type imaging photometric method adopted in the impurity concentration testing apparatus in the embodiment according to the present invention.

The following is an explanation of the other photometric optical system that adopts the non-scanning-type imaging method. FIG. 5 schematically illustrates the non-scanning-type imaging photometric method. As shown in the figure, the beam diameter of the terahertz pulse light beam is expanded to obtain an expanded light flux which is then irradiated in a batch over the entirety of a semiconductor material 15 to obtain transmitted images in this method. The electric field intensity distribution within the X-Y plane of transmitted pulse light having been transmitted through the semiconductor material 15 is measured in a batch by employing an imaging camera 16 (an image-forming optical system+a two-dimensional image capturing device). The advantage of this method is that since it is not necessary to move the test-piece (the semiconductor material 15) by utilizing a mechanical scanning system, transmitted images can be obtained within a very short period of time.

By measuring the electric field intensity distribution within the X-Y plane while changing the timing Δt with which a sampling pulse is transmitted from the time-delay device (not shown) to the imaging camera 16, time-series transmitted images are obtained. The resulting time-series transmitted images are stored in a storage device (not shown). By implementing a Fourier transform operation similar to that performed in the scanning imaging photometric method on the time-series transmitted images, a two-dimensional transmitted image (spectral image) is obtained. In addition, by performing a linear conversion operation such as Radon conversion at the computer on a plurality of two-dimensional projected images obtained by varying the angle at which the terahertz pulse light beam is irradiated on the semiconductor material 15, a three-dimensional sectioned image can be obtained.

Figure 6:
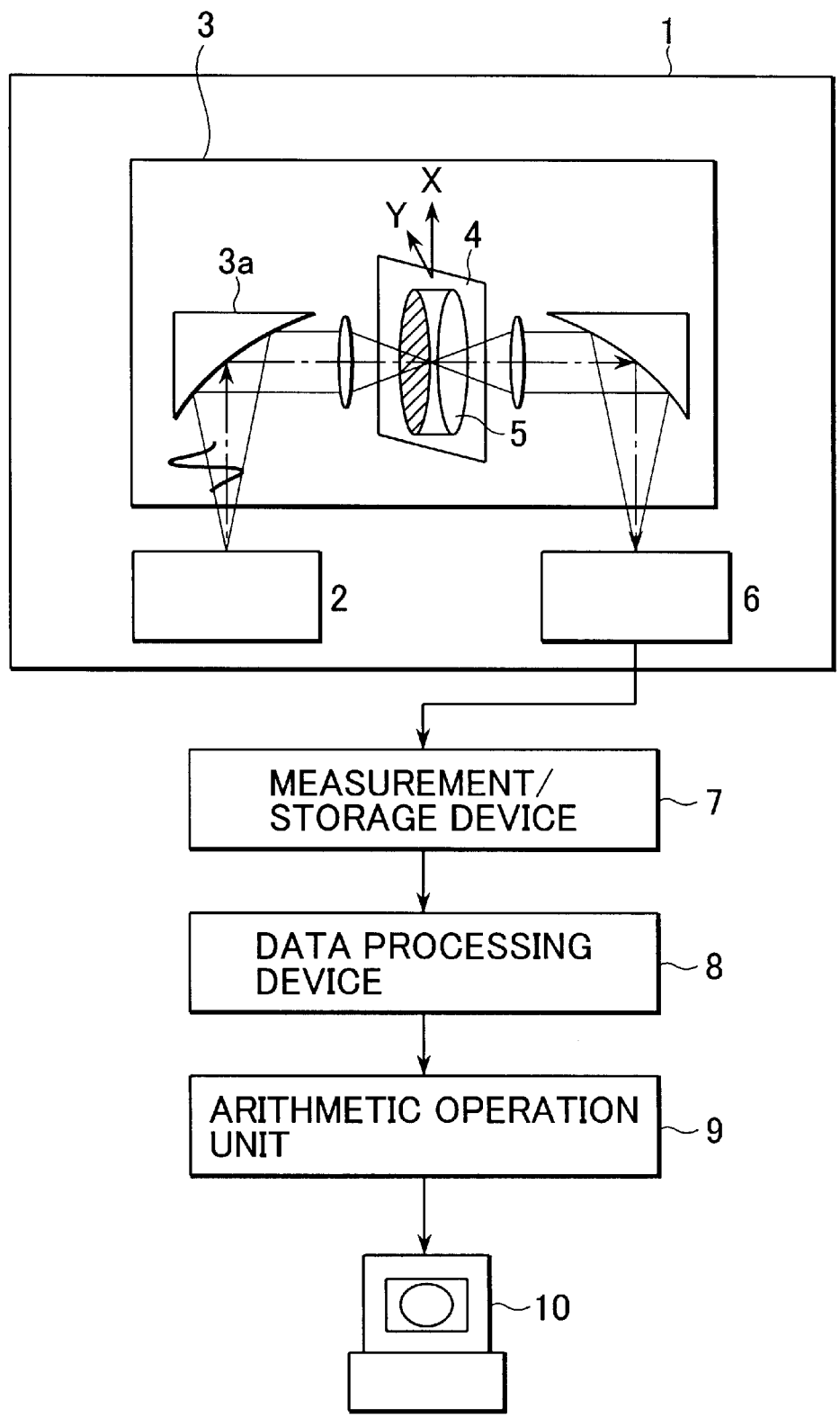
FIG. 6 is an overall block diagram of the impurity concentration testing apparatus adopting the scanning-type imaging photometric method in the embodiment of the present invention.

The primary components constituting the impurity concentration testing apparatus according to the present invention are now explained. FIG. 6 shows the overall structure of the impurity concentration testing apparatus according to the present invention which adopts the scanning imaging method. The terahertz pulse light source 2, a test-piece chamber 3 and the terahertz pulse detector 6 are provided in a measurement chamber 1. In the test-piece chamber 3, an X-Y stage 4 that moves a photometric optical system 3a and the semiconductor material 5 over a two-dimensional plane is provided.

Terahertz pulse light emitted from the terahertz pulse light source 2, which then becomes a condensed light flux at the photometric optical system 3a is irradiated on one point of the semiconductor material 5. The irradiated terahertz pulse light is transmitted through the semiconductor material 5 and enters the terahertz pulse detector 6. As explained earlier, the X-Y stage 4 is employed to perform X-Y scanning of the semiconductor material 5 placed on the X-Y stage 4 in order to obtain a two-dimensional projected image of the semiconductor material 5. As the X-Y scanning implemented by the X-Y stage 4 progresses, the terahertz pulse detector 6 sequentially detects the transmitted pulse light and sends signals indicating the electric field intensity levels to a measurement/storage device 7.

The measurement/storage device 7 measures a time-series signal indicating the electric field intensity of the terahertz pulse light for each pixel and stores it in memory. A data processing device 8 performs an arithmetic operation through which the time-series signal corresponding to each pixel undergoes a Fourier transform to be converted to a frequency spectrum, and calculates the spectral transmittance.

An arithmetic operation unit 9 calculates the oxygen concentration, the nitrogen concentration and the carbon concentration in the semiconductor material 5 based upon the frequency dependency of the spectral transmittance calculated at the data processing device 8, by adopting Lambert's light absorption theory. An image processing device 10 restructures the numerical value data corresponding to the individual pixels calculated at the arithmetic operation unit 9 on a computer and generates a two-dimensional image based upon the restructured data. In addition, the image processing device 10 performs a linear conversion operation to synthesize a three-dimensional sectioned image from a plurality of two-dimensional projected images.

Figure 7:
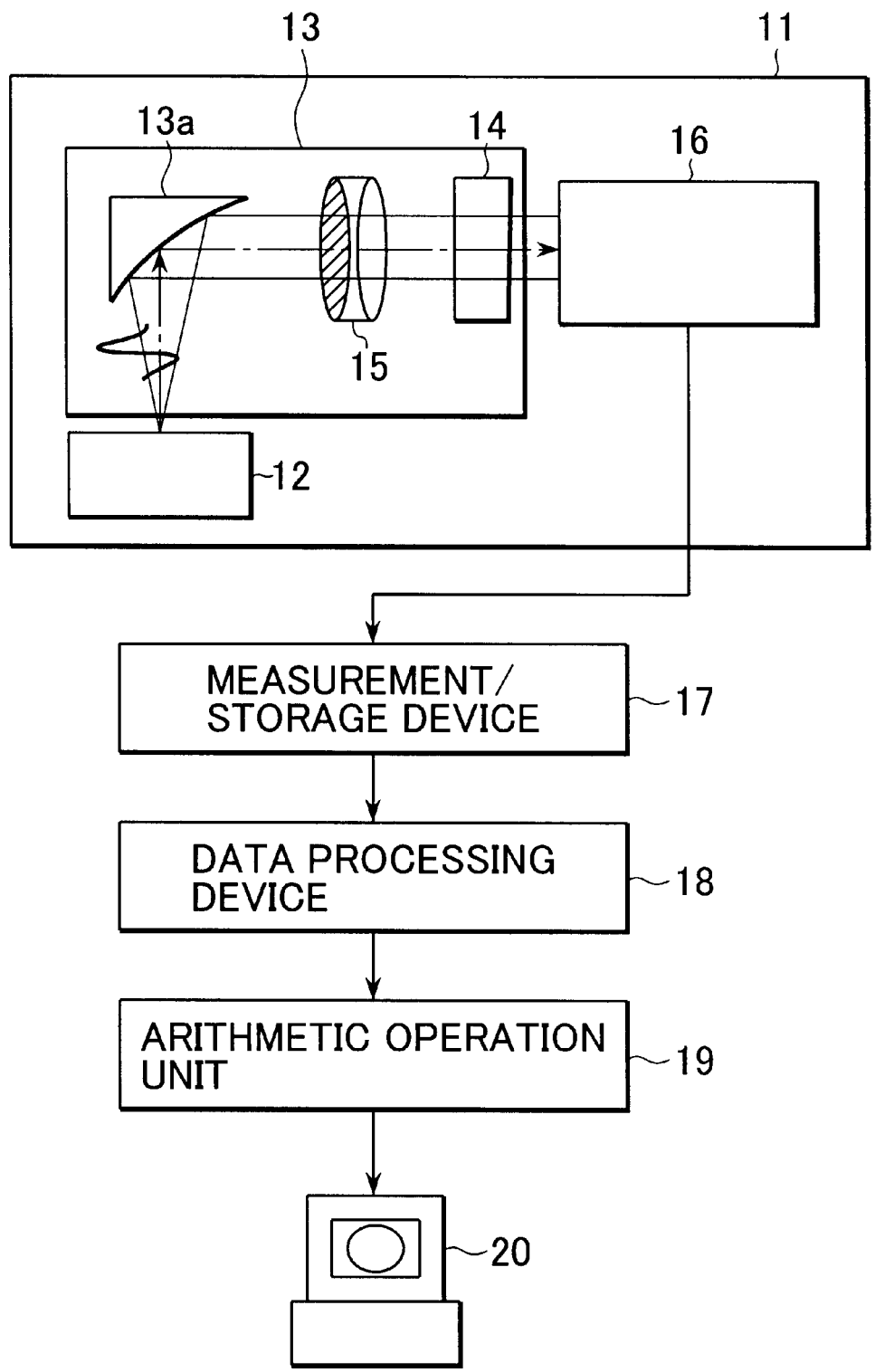
FIG. 7 is an overall block diagram of the impurity concentration testing apparatus adopting the non-scanning-type imaging photometric method in the embodiment of the present invention.

FIG. 7 illustrates the overall structure of the impurity concentration testing apparatus according to the present invention which adopts the non-scanning-type imaging method. In a measurement chamber 11, a terahertz pulse light source 12, a test-piece chamber 13 and an image detector 16 are provided. A photometric optical system 13*a* and an image-forming optical system 14 that forms an image of transmitted pulse light having been transmitted through the semiconductor material 15 are provided at test-piece chamber 13. These optical systems are provided to obtain in a batch two-dimensional projected images of the semiconductor material 15 in the terahertz frequency range.

Terahertz pulse light generated from the terahertz pulse light source 12 becomes an expanded light flux at the photometric optical system 13*a* and is irradiated in a batch over the entire semiconductor material 15. It is then transmitted through the semiconductor material 15, an image of the transmitted light is formed at the image-forming optical system 14, and the light flux then enters the image detector 16. At the image detector 16, a plurality of light-receiving elements are arrayed over an area the size of which allows the transmitted pulse light to be detected in a batch. Electric field intensity signals output from the individual light-receiving elements at the image detector 16 are provided to a measurement/storage device 17.

The measurement/storage device 17 measures and stores in memory a time-series waveform of the electric field intensity of the terahertz pulse light detected by the image detector 16. A data processing device 18 obtains a spectral transmittance image by converting the time-series waveform to a frequency spectrum through a Fourier transform operation performed on the time-series waveform in units of individual light-receiving elements, i.e., the individual pixels, at the image detector 16.

An arithmetic operation unit 19 calculates the oxygen concentration, the nitrogen concentration and the carbon concentration in the semiconductor material 15 by using the spectral image, based upon Lambert's light absorption theory. An image processing device 20 obtains a two-dimensional projected image based upon the numerical value data obtained at the arithmetic operation unit 19. In addition, the image processing device 20 performs digital image processing on the two-dimensional projected image by employing a computer to reproduce a three-dimensional sectioned image inside the semiconductor material.

Impurities in a semiconductor material are known to achieve inherent localized oscillation modes. Light is absorbed in an optically active localized oscillation mode achieved by the impurities in the semiconductor including oxygen located at the entry position, the nitrogen in the molecular form and the carbon at the substitution position. The value of the coefficient of the light absorption attributable to the localized oscillation modes is known to change in proportion to the concentration of the impurities contained in a semiconductor material. The concentration of an impurity in the semiconductor material can be calculated by measuring the corresponding light absorption coefficient (refer to Chapter 6 of "Semiconductor Silicon Crystal Engineering" by Fumio Shimura, published by Maruzen).

Now, the analysis method employed to calculate the oxygen concentration, the nitrogen concentration and the carbon concentration in a semiconductor material by using the apparatus described above is explained in reference to FIGS. 8A, 8B and 9.

Figure 8A:
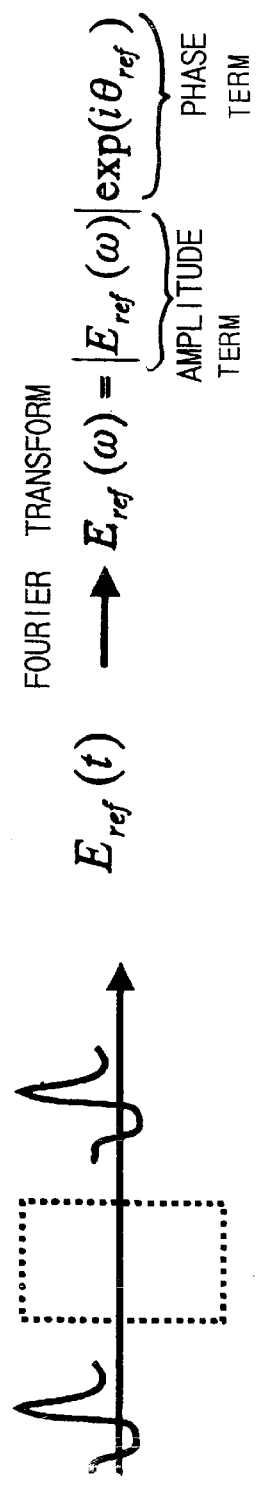
FIGS. 8A and 8B illustrate the principle of the analysis method adopted in the impurity concentration testing apparatus in the embodiment of the present invention.
Figure 8B:
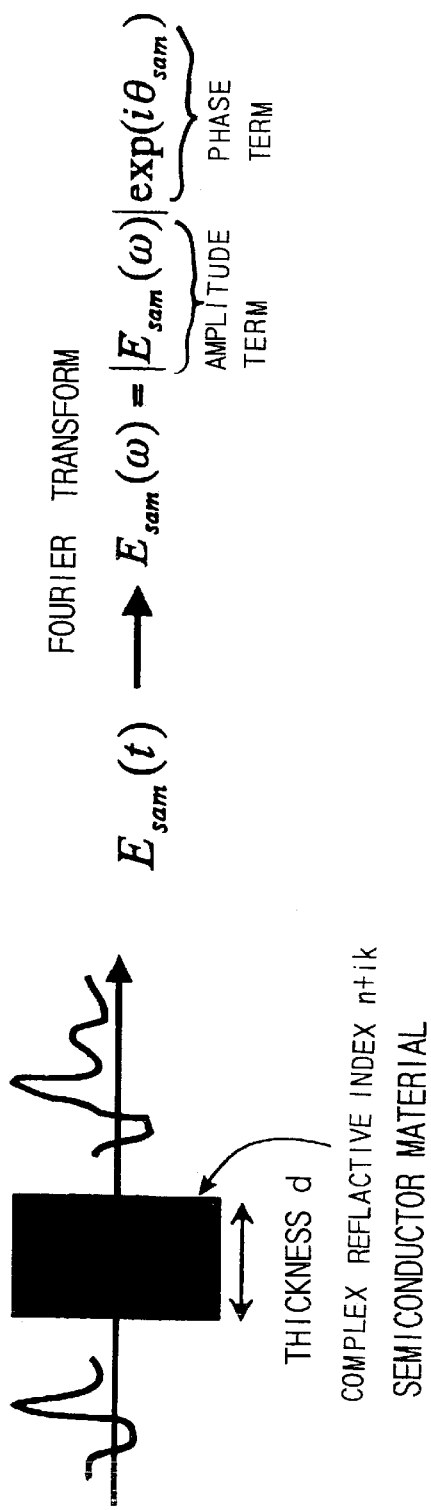
Figure 9:
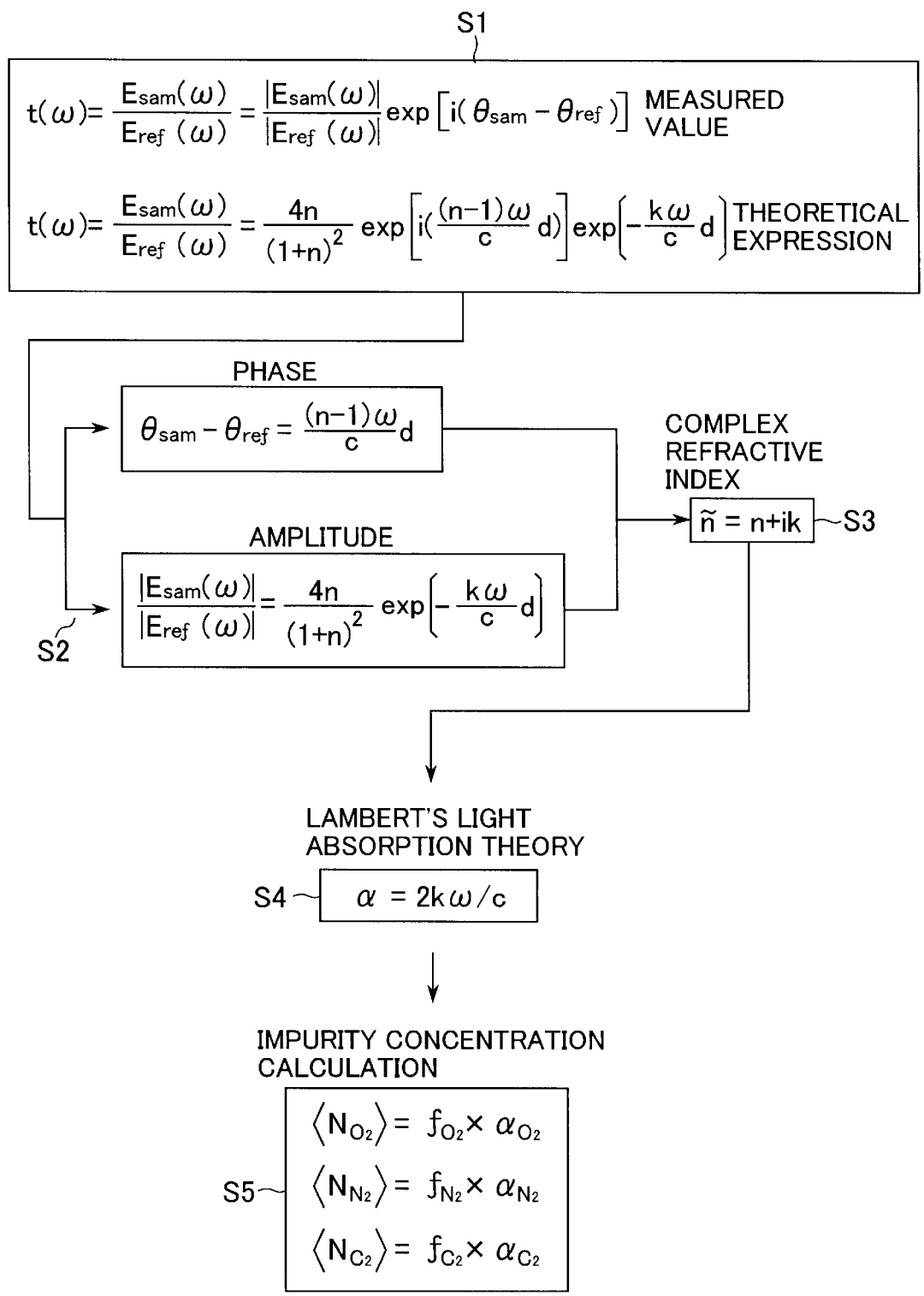
FIG. 9 presents a process diagram of the analysis method adopted in the impurity concentration testing apparatus in the embodiment of the present invention.

FIGS. 8A and 8B illustrate a process implemented in the analysis method adopted in the impurity concentration testing apparatus according to the present invention. FIG. 9 is a process diagram illustrating the procedure implemented in the analysis method to calculate the impurity concentration (the oxygen concentration, the nitrogen concentration and the carbon concentration) in the semiconductor material. For purposes of simplification, the method is explained by focusing on the process implemented on a single pixel.

Terahertz pulse light is irradiated on one point (equivalent to one pixel) of the semiconductor material and a time-series waveform E(t) of the electric field intensity of the transmitted pulse light having been transmitted through the semiconductor material is recorded. By performing a Fourier transform on the time-series waveform E(t) of the electric field intensity, the amplitude and the phase of the pulse light are calculated. The relationship among the time-series waveform E(t), the light amplitude E($\omega$) and the light phase $\theta$ is defined through the Fourier transform presented in the following formula (1).

$$E(\omega) = \int_{-\infty}^{\infty} E(t)\exp(-i\omega t)dt = |E(\omega)|\exp(i\theta) \quad (1)$$

When performing a measuring operation, first, a time-series waveform Eref(t) is measured without inserting the semiconductor material (measurement target) in the optical path of the photometric optical system as shown in FIG. 8A. The time-series waveform Eref(t) thus measured then undergoes a Fourier transform and, as a result, a reference amplitude |Eref($\omega$)| and a reference phase $\theta$ref are obtained. Next, as shown in FIG. 8B, a time-series waveform Esam(t) is measured with the semiconductor material inserted in the optical path of the photometric optical system. By performing a Fourier transform on the measured time-series waveform Esam(t), an amplitude |Esam($\omega$)| and a phase $\theta$sam manifesting when the measurement target is inserted in the optical system are ascertained.

The complex amplitude transmittance t($\omega$) of the semiconductor material is defined as expressed in the following formula (2) (FIG. 9 S1). Esam($\omega$) and Eref($\omega$) respectively represent the ratio of the Fourier components of the electric field intensity of the pulse light obtained by inserting and without inserting the semiconductor material in the optical path of the photometric optical system, which are actually measured (see FIGS. 8A and 8B).

$$t(\omega) = \frac{E_{sam}(\omega)}{E_{ref}(\omega)} = \frac{|E_{sam}(\omega)|}{|E_{ref}(\omega)|}\exp[i(\theta_{sam} - \theta_{ref})] \quad (2)$$

With n+ik representing the complex refractive index of the semiconductor material, the theoretical complex amplitude transmittance t($\omega$) manifesting when the semiconductor material having a thickness d is inserted in the optical path is calculated through the following formula (3) (FIG. 9 S1). It is to be noted that c represents light speed.

$$t(\omega) = \frac{E_{sam}(\omega)}{E_{ref}(\omega)} \quad (3)$$

$$= \frac{4n}{(1+n)^2} \exp\left[i\left(\frac{(n-1)\omega}{c}d\right)\right] \exp\left(-\frac{k\omega}{c}d\right)$$

By comparing formulae (2) and (3) above, the following formulae (4) and (5) are obtained (FIG. 9 S2).

$$\theta_{sam} - \theta_{ref} = \frac{(n-1)\omega}{c}d \quad (4)$$

$$\frac{|E_{sam}(\omega)|}{|E_{ref}(\omega)|} = \frac{4n}{(1+n)^2} \exp\left(-\frac{k\omega}{c}d\right) \quad (5)$$

Since the left-hand side members of formulae (4) and (5) are each constituted of a measured quantity, the value of n can be calculated through formula (4) as long as the thickness d of the semiconductor material is known. Using the calculated value of n, the value of k can be calculated through formula (5). Namely, the complex refractive index n+ik of the semiconductor material can be ascertained.

The measuring device is capable of directly measuring information related to the amplitude and the phase of light without having to measure the intensity of the light (i.e., the square of the electric field) as in the conventional light measurement (see B. B. Hu and M. C. Nuss, OPTICS LETTERS Vol. 20, No. 16, p1716, (1995)). For this reason, the complex refractive index n+ik of the semiconductor material can be calculated without engaging in a complicated calculation performed by using Kramers-Kronig relational formula (see "Basics of Optical Material Characteristics" by Keiei Kudo, published by Ohm Publishing House) (FIG. 9 S3). The light absorption coefficient α can be expressed as in formula (6) by using the imaginary part k of the complex refractive index n+ik, based upon a theory on the propagation of light inside an absorptive medium (see "Semiconductor Evaluation Technology" by Takashi Katoda, published by Sangyo Tosho) (see FIG. 9 S4).

$$\alpha = 2kw/c \quad (6)$$

Thus, since the imaginary part k in the complex refractive index can be actually measured through the spectral measurement, the light absorption coefficient a can be calculated. In addition, by multiplying the light absorption coefficient α by an appropriate conversion coefficient f, the oxygen concentration, the nitrogen concentration and the carbon concentration can be individually calculated as expressed in formulae (7)–(9) (FIG. 9 S5).

$$<No_2> = fo_2 \times \alpha o_2 \quad (7)$$

$$<Nn_2> = fn_2 \times \alpha n_2 \quad (8)$$

$$<Nc_2> = fc_2 \times \alpha c_2 \quad (9)$$

Figure 10:
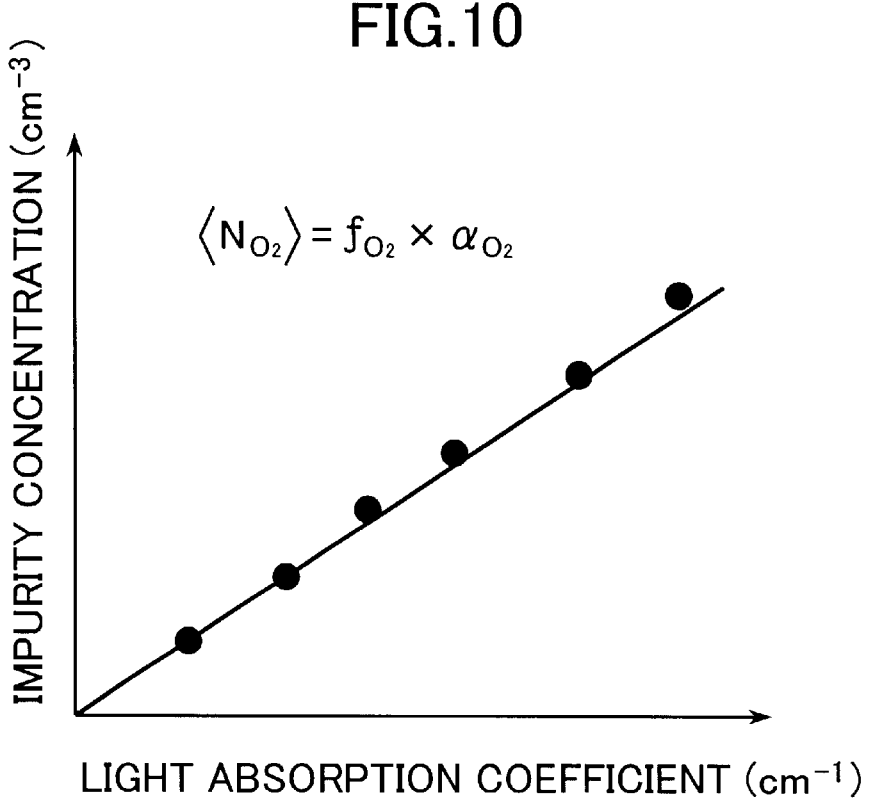
FIG. 10 presents a graph illustrating the relationship between an impurity concentration and the light absorption coefficient.

The conversion coefficient f is a value obtained through testing, which may be ascertained by measuring the light absorption coefficient α of a semiconductor material having a known impurity concentration and drawing a calibration curve. FIG. 10 presents a graph (calibration curve) of the relationship between an impurity concentration and the light absorption coefficient. The calibration curve is obtained by plotting the measured values of the light absorption coefficient corresponding to known values of oxygen concentration. The inclination of the calibration curve is the conversion coefficient f. The impurity concentration is ascertained by measuring the light absorption coefficient of a given semiconductor material and multiplying the light absorption coefficient by the conversion coefficient f.

By converting the numerical value data of the impurity concentration obtained through the procedure described above to an image with variable-density or to a color image, a two-dimensional projected image of the impurity concentration distribution in the semiconductor material is obtained. By varying the angle at which the terahertz pulse light is irradiated on the semiconductor material to obtain a plurality of two-dimensional projected images and performing a linear conversion operation such as Radon conversion on the two-dimensional projected images, a three-dimensional sectioned image of the impurity concentration distribution in the semiconductor material is obtained.

The following is an explanation of a specific example in which a two-dimensional projected image of the impurity concentration distribution in a semiconductor material is obtained by employing the impurity concentration testing apparatus according to the present invention.

Figure 11:
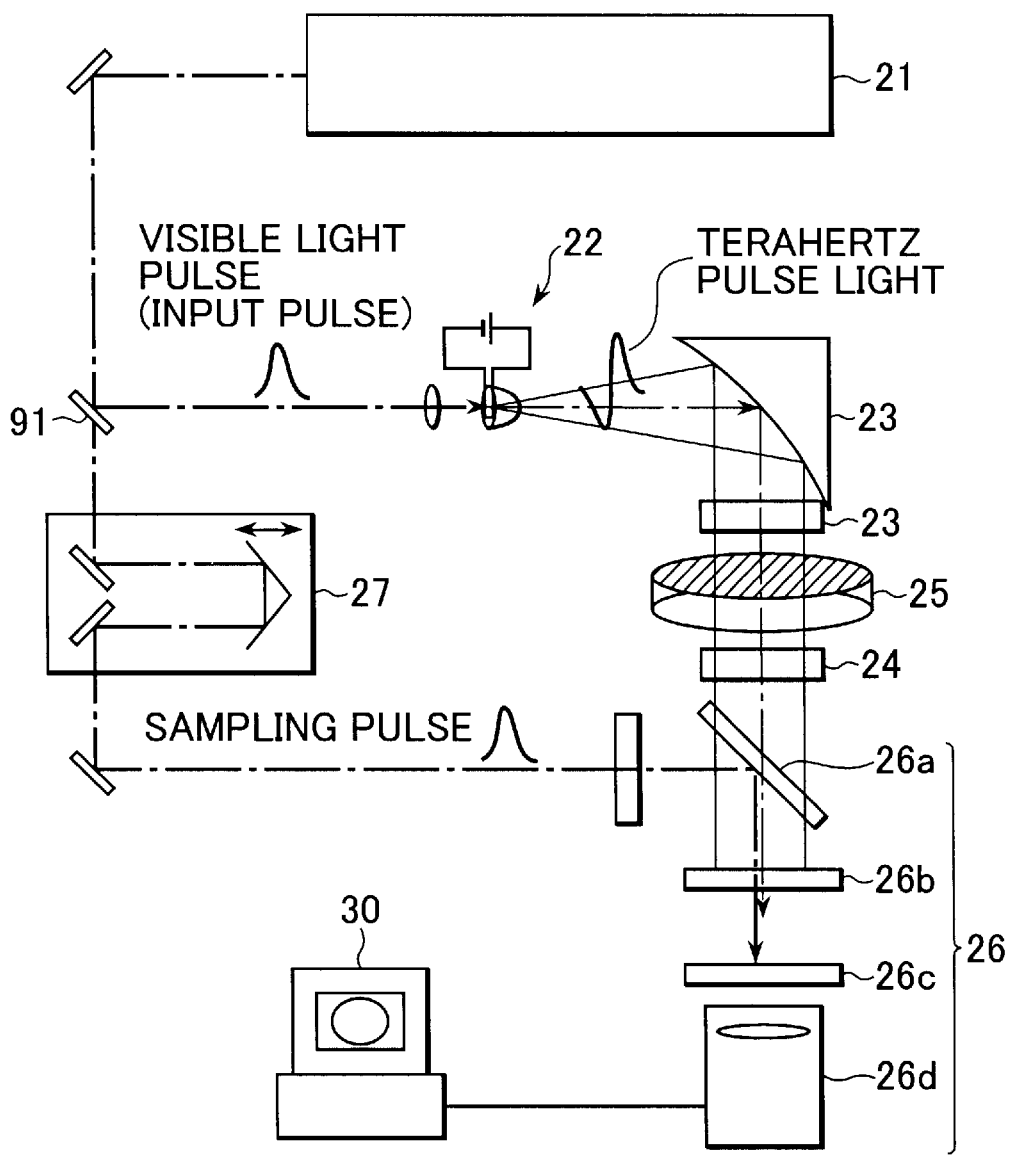
FIG. 11 is an overall view of the impurity concentration testing apparatus adopting the non-scanning-type imaging photometric method in the embodiment of the present invention.

FIG. 11 shows the components constituting the impurity concentration testing apparatus in an embodiment of the present invention that adopts the non-scanning-type imaging method. A terahertz pulse light beam is irradiated in a batch over the entire surface of a semiconductor wafer 25. A terahertz pulse light source 22 is normally constituted of a semiconductor photoconductive switch device. The semiconductor photoconductive switch device is constituted by forming a metal antenna on a semiconductor material that is capable of engaging in fast optical response when irradiated with a visible light pulse from a visible light pulse laser 21. The visible light pulse from the visible light pulse laser 21 is the "input pulse" mentioned earlier. By irradiating the visible light pulse on the terahertz pulse light source 22, terahertz pulse light is radiated. Terahertz pulse light may otherwise be generated by irradiating a visible light pulse on a compound semiconductor.

A terahertz optical element 23 constituting the photometric optical system is formed by using at least one of; a mirror deposited with aluminum, a mirror deposited with gold, a mirror deposited with silver, a silicon lens, a germanium lens, a polyethylene lens, a wire grid and the like, that have undergone an oxidation inhibiting treatment. Transmitted pulse light having been transmitted through the semiconductor wafer 25 is then transmitted through an imageforming optical system 24 before entering an image detector 26.

The image detector 26 includes a beam-splitter mirror 26a, an imaging plate 26b, a polarizer 26c and an invisible light CCD camera 26d and the like. The beam-splitter mirror 26a may be constituted of a silicon plate or a pericle. The imaging plate 26b may be constituted of an electro-optic crystal of a semiconductor or a dielectric material. A wave plate may be utilized in place of the polarizer 26c.

The length of time required for the measurement is greatly reduced by adopting the non-scanning-type imaging method since the pulse light transmitted through the semiconductor wafer 25 can be converted to a two-dimensional image with the image-forming optical system 24. A problem of the non-scanning-type imaging method lies in the image detector (two-dimensional image-capturing device) that detects terahertz pulse light and, at present, there is no two-dimensional image-capturing device capable of directly receiving terahertz pulse light. However, real time terahertz imaging is enabled by adopting the electro-optic sampling method disclosed in a publication (Q. Wu et al. Appl. Phys. Lett. 69 Vol 69, No.8, p.1026 (1996)).

In principle, a terahertz transmitted image of a semiconductor material is displayed on an imaging plate 26b constituted of an electro-optic crystal and the terahertz light image information is read out and the terahertz light image information is converted to polarization information of visible light which is then rendered to an image by taking advantage of Pockel's effect through the method. Pockel's effect refers to an effect whereby the refractive index of the electro-optic crystal changes in proportion to the electric field intensity of the terahertz pulse light. In the actual application, visible light image information generated by utilizing the beam-splitter mirror 26a, the imaging plate 26b and the polarizer 26c is recorded by the two-dimensional image capturing device (such as a CCD camera), as shown in FIG. 11 The measurement of the change occurring over time in the transmitted image is implemented through the following procedure. As shown in FIG. 11, the visible light pulse from the visible light pulse laser 21 is branched. One branch of the visible light pulse travels through a time-delay movable mirror 27 and is input to the imaging plate 26b as a sampling pulse. The instant the sampling pulse is input, the other branch of the visible light pulse, which has been branched at a half mirror 91 and has been transmitted through the semiconductor wafer 25, i.e., the transmitted image, is taken into the visible light CCD camera 26d as an image. The image taken in at this time is the transmitted image corresponding to the time point t0.

Next, the time-delay movable mirror 27 is moved and a transmitted image is taken in with the time point at which the sampling pulse is input to the imaging plate 26b set to t0+Δt. By repeating this step k times while changing Δt, transmitted images over the time span ranging from t0 through tk are taken into the visible light CCD camera 26d. The numerical value data of the transmitted images are stored at the measurement/storage device. By viewing the numerical value data corresponding to a single pixel aij along the time axis, as shown in FIG. 3A, a time-series waveform of the electric field intensity of the terahertz pulse light is obtained.

Figure 12:
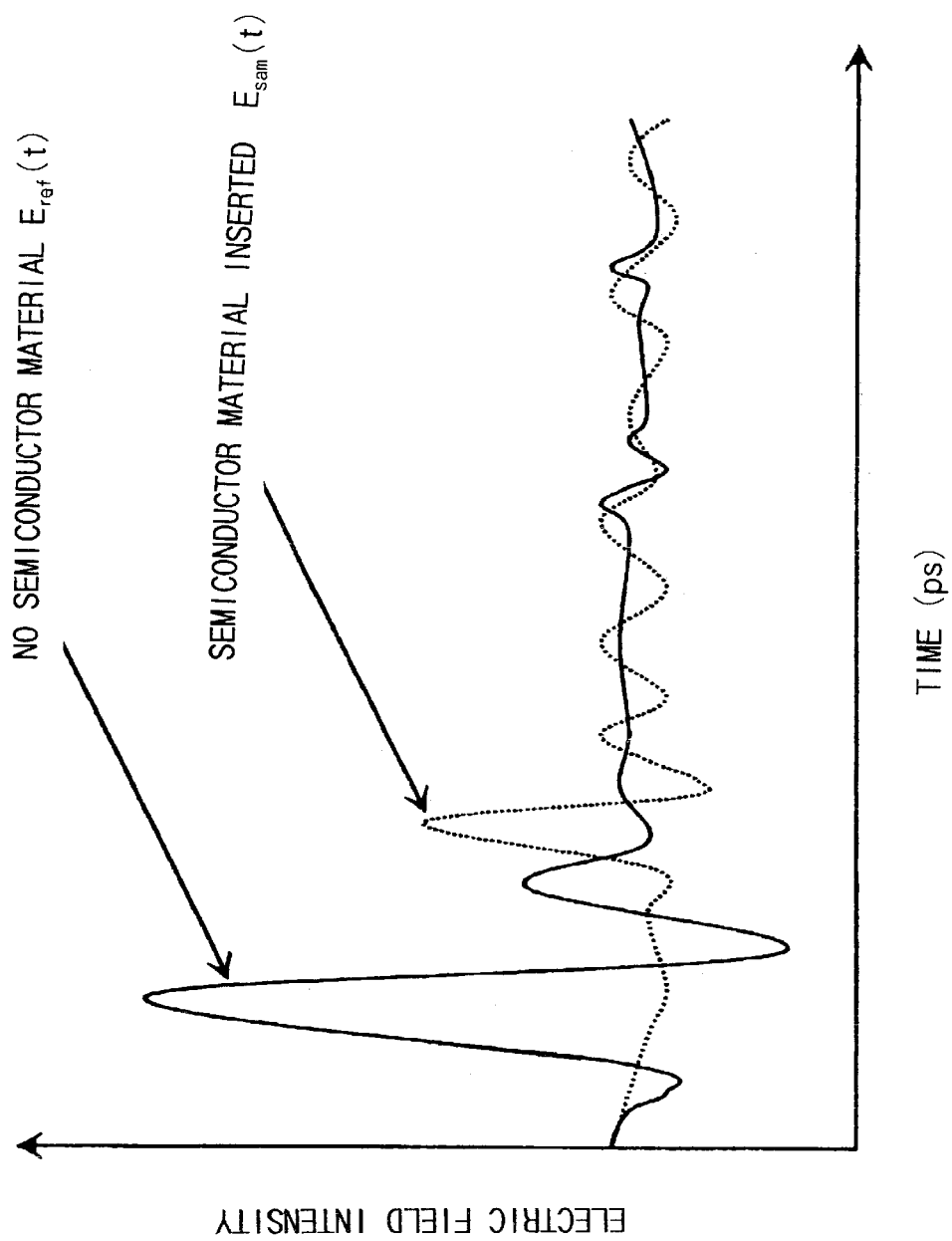
FIG. 12 shows a time-series waveform of the electric field intensity obtained in the impurity concentration testing apparatus in the embodiment of the present invention.

FIG. 12 presents an example of the time-series waveform of the electric field intensity. The two curves represent the waveforms, one of which manifests when the semiconductor material is inserted in the optical path of the terahertz pulse light and the other of which manifests when the semiconductor material is not inserted in the optical path. By performing a Fourier transform on these time-series waveforms, a frequency dependency of the amplitude and the phase of the electric field defined through formula (1) is ascertained as shown in FIG. 13.

Figure 13:
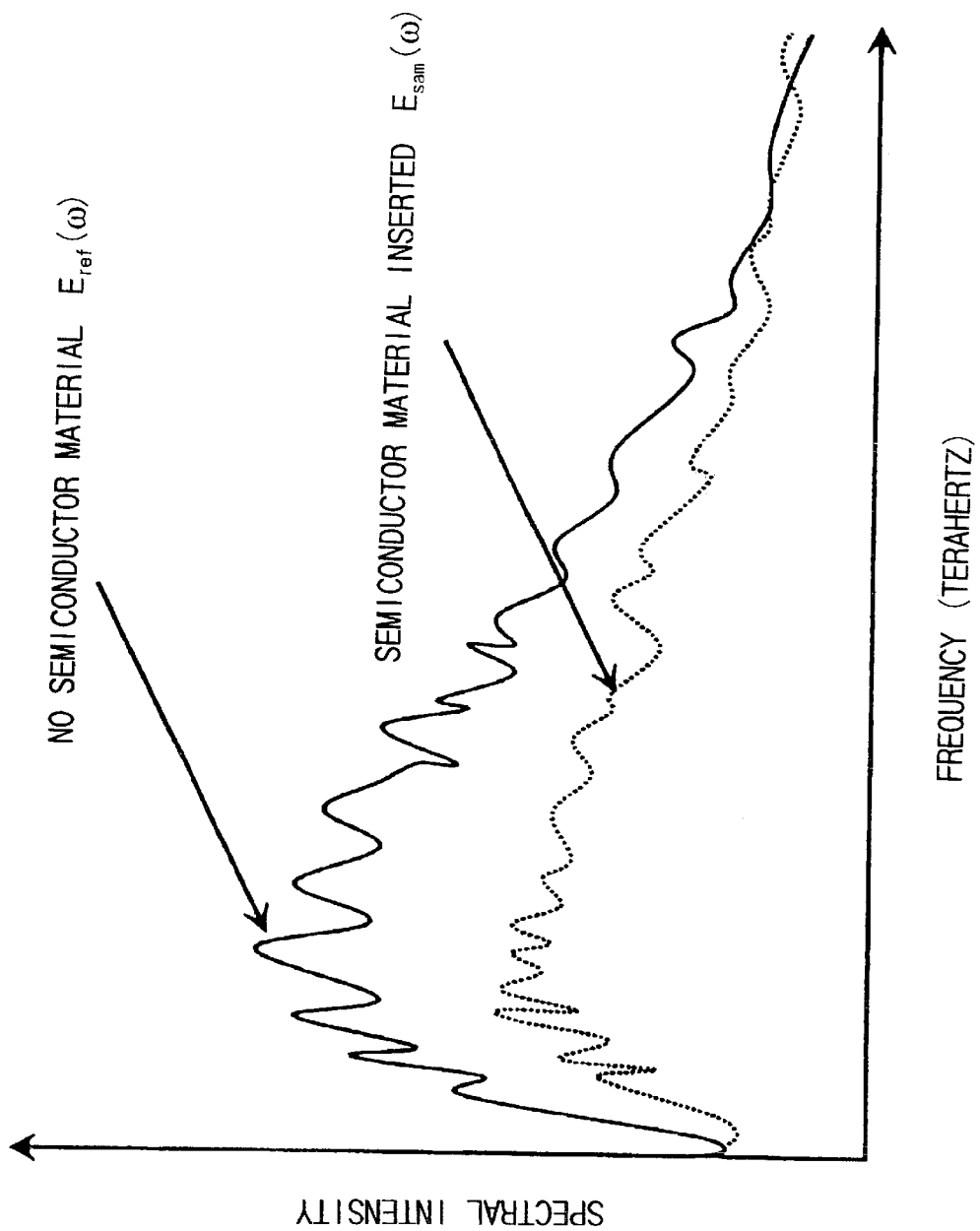
FIG. 13 presents a graph of the frequency dependency of the spectral intensity measured in the impurity concentration testing apparatus in the embodiment of the present invention.

FIG. 13 presents a graph of the frequency dependency of the electric field intensity, with the two curves representing the spectrum waveforms achieved when the semiconductor material is inserted in the optical path of the terahertz pulse light and when the semiconductor material is not inserted in the optical path.

The frequency characteristics of the amplitude and the phase are also ascertained in a similar manner. During the measurement process, a time-series waveform Eref(t) is first measured without inserting the semiconductor material in the optical path and an amplitude |Eref(ω)| and a phase θref for reference are calculated through a Fourier transform performed on the time-series waveform Eref(t). Next, the time-series waveform Esam(t) is first measured by inserting the semiconductor material constituting the measurement target in the optical path and an amplitude |Esam(ω)| and a phase θsam are obtained through a Fourier transform performed on the time-series waveform Esam(t). By incorporating the measured values of |Eref(ω)|, |Esam(ω)|, θref and θsam in formulae (10) and (11) (modified versions of formulae (4) and (5)) for substitution, the complex refractive index n+ik is ascertained.

$$n = \frac{(\theta_{sam} - \theta_{ref})}{d} \frac{c}{\omega} + 1 \quad (10)$$

$$k = -\frac{c}{\omega d} \ln\left[\frac{(1+n)^2}{4n} \frac{|E_{sam}(\omega)|}{|E_{ref}(\omega)|}\right] \quad (11)$$

By incorporating the imaginary part k of the complex refractive index calculated through formula (11) in formula (6) for substitution, the light absorption coefficient a is ascertained. Once the light absorption coefficient a is ascertained, the impurity concentration with regard to oxygen, nitrogen and carbon are individually calculated through formulae (7)–(9). By displaying the values of the impurity concentration thus ascertained as an image with variable-density or a color image, a two-dimensional projected image is obtained.

Figure 14:
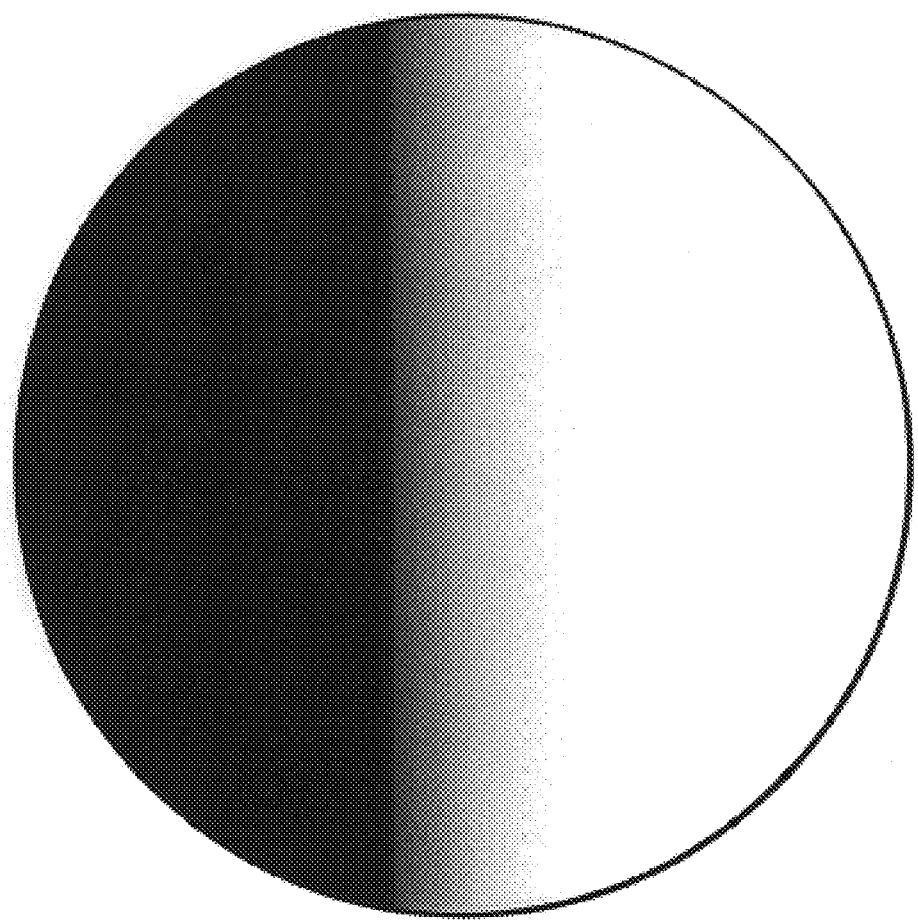
FIG. 14 shows an image of the impurity concentration distribution obtained in the impurity concentration testing apparatus in the embodiment of the present invention.

The impurity concentration testing apparatus according to the present invention, which enables immediate imaging of the impurity concentration distribution in a semiconductor material makes it possible to perform a test in real time. FIG. 14 presents a two-dimensional projected image achieved by implementing variable-density image processing on an impurity concentration distribution of a semiconductor wafer containing impurities. Impurities are added in the left half of the semiconductor wafer in FIG. 14 while no impurities are present in the right half. As the figure clearly shows, the difference between the area where impurities are added and the area where no impurities are present can be two-dimensionally observed.

In addition, by adopting Lambert's analysis method, the light absorption coefficient can be easily calculated based upon the complex refractive index of the semiconductor material. Since the impurity concentration in the semiconductor can be calculated by using the light absorption coefficient thus calculated, easy, real-time measurement and evaluation are enabled without damaging or contacting the semiconductor material. Furthermore, since a two-dimensional image as the spatial distribution of the impurity concentration is achieved, a reduction in the length of time required for testing is achieved.

What is claimed is:

1. A semiconductor impurity concentration testing apparatus, comprising:
    a terahertz pulse light source that irradiates terahertz pulse light on a specimen;
    a light detector that detects transmitted pulse light having been transmitted through the specimen;
    a terahertz time domain measurement device that measures a spectral transmittance based upon a time-series waveform of an electric field intensity of the transmitted pulse light detected by said light detector; and
    an arithmetic operation unit that calculates a complex refractive index of the specimen based upon the measurement value of the spectral transmittance and a theoretical value of the spectral transmittance, calculates a light absorption coefficient of the specimen with the complex refractive index based upon Lambert's light absorption theory and calculates an impurity concentration in the specimen based upon the light absorption coefficient, wherein;
    said arithmetic operation unit, obtaining a conversion coefficient between the impurity concentration and the light absorption coefficient in advance by measuring the light absorption coefficient of the specimen with known impurity concentration, calculates the impurity concentration in the specimen based upon the calculated light absorption coefficient and the conversion coefficient.

2. A semiconductor impurity concentration testing apparatus, comprising:

a terahertz pulse light source that irradiates terahertz pulse light on a semiconductor material;

a light detector that detects transmitted pulse light having been transmitted through the semiconductor material;

a terahertz time domain measurement device that obtains a spectral transmittance based upon an amplitude and a phase of the transmitted pulse light calculated by performing a Fourier transform on a time-series waveform of an electric field intensity of the transmitted pulse light detected by said light detector; and an arithmetic operation unit that calculates an impurity concentration in the semiconductor material based upon said spectral transmittance, wherein:

said terahertz time domain measurement device operates (1) a first step in which a time-series waveform of the electric field intensity of the transmitted pulse light obtained by inserting the semiconductor material in an optical path and a time-series waveform of the electric field intensity obtained without inserting the semiconductor material in the optical path are respectively obtained, and an amplitude and a phase of the transmitted pulse light are calculated by performing a Fourier transform on each of the time-series waveforms and (2) a second step in which a measurement value of a complex amplitude transmittance as the spectral transmittance is calculated based upon a ratio of the Fourier components of the time-series waveform obtained by inserting and without inserting the semiconductor material in the optical path;

said arithmetic operation unit operates (1) a third step in which a complex refractive index of the semiconductor material is calculated based upon a theoretical value of a complex amplitude transmittance which is equivalent to a value obtained by inserting the semiconductor material in the optical path and the measurement value of the complex amplitude transmittance and (2) a fourth step in which a light absorption coefficient of the semiconductor material is calculated with the complex refractive index based upon Lambert's light absorption theory;

the light absorption coefficient of the semiconductor material with known impurity concentration is calculated by performing the first step through the fourth step;

the light absorption coefficient of the semiconductor material to be tested is calculated by performing the first step through the fourth step; and said arithmetic operation unit calculates a conversion coefficient between the impurity concentration and the calculated light absorption coefficient of the semiconductor material with known impurity concentration and calculates the impurity concentration in the semiconductor material to be tested based upon the calculated light absorption coefficient of the semiconductor material to be tested and the conversion coefficient.

3. A semiconductor impurity concentration testing method comprising:

expanding a light flux of terahertz pulse light and irradiating in a batch the expanded light flux over an entire surface of a semiconductor material;

detecting in a batch transmitted pulse light having been transmitted through the semiconductor material irradiated with the expanded light flux;

calculating a spectral transmittance based upon a time-series waveform of an electric field intensity of the transmitted pulse light;

calculating an impurity concentration in the semiconductor material based upon the spectral transmittance;

a first step in which time-series waveforms of the electric field intensity of the transmitted pulse light obtained by inserting and without inserting a semiconductor material with known impurity concentration in an optical path are respectively obtained, and an amplitude and a phase of the transmitted pulse light are calculated by performing a Fourier transform on each of the time-series waveforms;

a second step in which a measurement value of a complex amplitude transmittance as the spectral transmittance is calculated based upon a ratio of the Fourier components of the time-series waveforms obtained by inserting and without inserting the semiconductor material with known impurity concentration in the optical path;

a third step in which a complex refractive index of the semiconductor material with known impurity concentration is calculated based upon a theoretical value of a complex amplitude transmittance which is equivalent to a value obtained by inserting the semiconductor material in the optical path and the measurement value of the complex amplitude transmittance;

a fourth step in which a light absorption coefficient of the semiconductor material with known impurity concentration is calculated with the complex refractive index based upon Lambert's light absorption theory; and a fifth step in which a conversion coefficient between the impurity concentration and the light absorption coefficient of the semiconductor material with known impurity concentration calculated in the fourth step is calculated, wherein:

in said step of calculating a spectral transmittance, (1) time-series waveforms of the electric field intensity of the transmitted pulse light obtained by inserting and without inserting a semiconductor material to be tested in an optical path are respectively obtained, and an amplitude and a phase of the transmitted pulse light are calculated by performing a Fourier transform on each of the time-series waveforms and (2) a measurement value of a complex amplitude transmittance as the spectral transmittance is calculated based upon a ratio of the Fourier components of the time-series waveforms obtained by inserting and without inserting the semiconductor material to be tested in the optical path; and in said step of calculating an impurity concentration, (1) a complex refractive index of the semiconductor material to be tested is calculated based upon a theoretical value of a complex amplitude transmittance which is equivalent to a value obtained by inserting the semiconductor material in the optical path and the measurement value of the complex amplitude transmittance, (2) a light absorption coefficient of the semiconductor material to be tested is calculated with the complex refractive index based upon Lambert's light absorption theory and (3) the impurity concentration in the semiconductor material to be tested is calculated based upon the light absorption coefficient of the semiconductor material to be tested and the conversion coefficient calculated in the fifth step.

4. A semiconductor impurity concentration testing method comprising:

expanding a light flux of terahertz pulse light and irradiating in a batch the expanded light flux over an entire surface of a semiconductor material;

detecting in a batch transmitted pulse light having been transmitted through the semiconductor material irradiated with the expanded light flux;

calculating a spectral transmittance based upon a time-series waveform of an electric field intensity of the transmitted pulse light; and calculating an impurity concentration in the semiconductor material based upon the spectral transmittance, wherein;

an analysis is executed based upon Lambert's light absorption theory to calculate an oxygen concentration a nitrogen concentration and a carbon concentration in the semiconductor material; and terahertz pulse light within a frequency range of 20 THz–80 THz is irradiated onto a semiconductor material when an oxygen concentration and a nitrogen concentration in the semiconductor material is calculated.

* * * * *